United States Patent [19]

Durdle et al.

[11] Patent Number: 5,955,879
[45] Date of Patent: Sep. 21, 1999

[54] METHOD AND DEVICE FOR MONITORING THE RELATIVE POSITIONS OF AT LEAST TWO FREELY MOVABLE POINTS AND PROVIDING FEEDBACK THEREFROM

[76] Inventors: Nelson G. Durdle, 4627—102 Avenue, Edmonton, Alberta, Canada, T6A 0P9; Edmond Lou, Apartment 301, 9730—106 Street, Edmonton, Alberta, Canada, T5K 1B7; V. James Raso, 12 Duncan Court, St. Albert, Alberta, Canada, T8N 4Z1; Douglas Hill, 10912—38 Avenue, Edmonton, Alberta, Canada, T6J 0K7

[21] Appl. No.: 08/730,877

[22] Filed: Oct. 18, 1996

Related U.S. Application Data

[60] Provisional application No. 60/005,732, Oct. 20, 1995.

[51] Int. Cl.$^6$ ............................. A61B 5/11; G01B 7/14; G01B 7/30
[52] U.S. Cl. ............................. 324/207.17; 324/207.25; 324/247; 340/551; 600/595; 702/153
[58] Field of Search ............................. 324/202, 207.17, 324/207.25, 207.26, 226, 247; 342/444, 445, 448, 463; 340/551, 552, 573; 600/409, 424, 595; 702/150–153

[56] References Cited

U.S. PATENT DOCUMENTS

| | | |
|---|---|---|
| 3,582,935 | 6/1971 | Verhaeghe . |
| 4,054,881 | 10/1977 | Raab ............................. 342/448 |
| 4,080,962 | 3/1978 | Berkeley . |
| 4,325,363 | 4/1982 | Berkeley . |
| 4,396,885 | 8/1983 | Constant ............................. 324/207.17 |
| 4,560,930 | 12/1985 | Kouno ............................. 324/247 X |
| 4,688,037 | 8/1987 | Krieg ............................. 324/247 X |
| 4,730,625 | 3/1988 | Fraser et al. . |
| 4,829,250 | 5/1989 | Rotier ............................. 324/207.17 X |
| 4,849,692 | 7/1989 | Blood . |
| 4,914,423 | 4/1990 | Fernandez . |
| 4,945,305 | 7/1990 | Blood . |
| 5,067,484 | 11/1991 | Hiemstra-Paez . |
| 5,086,290 | 2/1992 | Murray et al. ............................. 340/531 X |
| 5,099,831 | 3/1992 | Freed . |
| 5,109,194 | 4/1992 | Cantaloube ............................. 324/207.17 |
| 5,176,706 | 1/1993 | Lee . |
| 5,307,072 | 4/1994 | Jones, Jr. ............................. 324/247 X |
| 5,425,367 | 6/1995 | Shapiro et al. ............................. 324/326 X |
| 5,433,201 | 7/1995 | Manthey ............................. 600/595 |
| 5,469,861 | 11/1995 | Piscopo et al. ............................. 600/595 X |
| 5,646,525 | 7/1997 | Gilboa ............................. 324/207.17 |
| 5,661,459 | 8/1997 | Belcher ............................. 340/573 |
| 5,744,953 | 4/1998 | Hansen ............................. 324/207.17 |

OTHER PUBLICATIONS

Cheng, D.K. "Field and Wave Electromagnetics," World Student Series 2nd Ed. Addison–Wesley, 1989, pp. 234–236, 239, 307.

Dworkin, B. et al. Behavioral method for the treatment of Idiopathic Scoliosis, Proc. Natl. Acad. Sci. USA, vol. 82, pp. 2493–2497, 1985.

(List continued on next page.)

*Primary Examiner*—Gerald Strecker
*Attorney, Agent, or Firm*—Rodman & Rodman

[57] ABSTRACT

A method and device for monitoring the position of a second point relative to a first point. A magnetic field is produced from the first point and received at the second point to produce an output signal therefrom. Preferably, the magnetic field is produced by a transmitter located at the first point and is received by a receiver located at the second point. The position of the first point relative to the second point is then determined by using the output signal. Preferably, the first point and the second point are both freely movable and therefore, both the transmitter and the receiver are mobile. As well, preferably both the first and second points are located on a human body. Finally, preferably, a feedback signal is produced for indicating the determined position of the second point relative to the first point. The determined position of the second point relative to the first point may be compared with a preset reference position such that the feedback signal indicates a discrepancy between the position of the second point relative to the first point and the preset reference position.

24 Claims, 10 Drawing Sheets

OTHER PUBLICATIONS

Emans, J. et al. "The Boston Brace System for Idiopathic Scoliosis–Follow–up Results in 295 Patients," Spine, vol. 11, No. 8, pp. 792–801, 1986.

Houghton, R. et al. "Monitoring True Brace Compliance," Proceedings of the 21st Meeting of the Scoliosis Research Society, Hamilton, Bermuda, Sep., p. 101, 1986.

Lehnert, C.S. "Introduction to the three–dimensional scoliosis treatment according to Schroth," Physiotherapy, vol. 78 No. 11, pp. 810–815, 1992.

Mahood, J.K. et al "Perceptions of Cosmetic Deformity in Scoliosis," Proceedings of the 2nd International Symposium on Three Dimensional Scoliotic Deformities, Pescara, Sep., pp. 239–242, 1994.

Price, C.T. et al "Nighttime Bracing for Adolescent Idiopathic Scoliosis with the Charleston Bending Brace," Spine vol. 15, No. 12, pp. 1294–1299, 1990.

Weiss, H.R. "The Progression of Idiopathic Scoliosis under the Influence of a Physiotherapy rehabilitation Programme" Physiotherapy, vol. 78, No. 11, pp. 815–821, 1992.

Ylikoski, M. et al. "Biological Factors and Predictability of Bracing in Adolescent Idiopathic Scoliosis," J Pediatric Orthopedics, vol. 9, pp. 680–683, 1989.

METHOD AND DEVICE FOR MONITORING THE RELATIVE POSITIONS OF AT LEAST TWO FREELY MOVABLE POINTS AND PROVIDING FEEDBACK THEREFROM

CROSS REFERENCE TO RELATED APPLICATION

This Application claims the benefit of United States of America Provisional Application Number 60/005,732 filed Oct. 20, 1995.

FIELD OF THE INVENTION

The present invention relates to a method and a device for monitoring and measuring the position or orientation of one or more objects or subjects and providing feedback with respect to the position or orientation, preferably in at least two dimensions. Further, the invention is related to a method and a device for monitoring and measuring the posture of a subject and providing feedback with respect to the subject's posture, such as by signaling when either a desirable or undesirable posture exists, so that a desirable posture can be established.

BACKGROUND OF THE INVENTION

Scoliosis, Which is an abnormal curvature of the spine coupled with vertebral rotation, is most commonly found in adolescent females This abnormal curvature and rotation causes deformity of the rib cage witch results in asymmetries of the trunk. In a previous study (Mahood,, J. K. et al. "Perceptions of Cosmetic Deformity in Scoliosis", Proceedings of the 2nd International Symposium on Three Dimensional Scoliotic Deformities, Pescara, September, pp. 239–242, 1994), seven features of scoliosis were identified: shoulder height and shoulder angle differences, pelvis asymmetry, decompensation, waist crease, scapula height difference and waist asymmetry. These identified features account for 85% of the overall impression of trunk deformity. Further, studies have established the repeatability and reliability of measuring surface features. In other words, these seven features can be reliably measured to provide an objective score of cosmetic deformity.

Clinicians have few non-surgical treatment tools for children with potentially progressive spinal deformities such as scoliosis. Brace treatment is most commonly used despite poor compliance and much uncertainty as to effectiveness (Houghton, R, et al. "Monitoring True Brace Compliance", Proceedings of the 21st Meeting of the Scoliosis Research Society, Hamilton, Bermuda, September, p. 101, 1986; Ylikkoski, M. et al. "Biological Factors and Predictability of Bracing in Adolescent Idiopathic Scoliosis", J Pediatric Orthopedics, Vol. 9, pp. 680–683, 1989). The Boston and Charleston braces are most frequently prescribed due to their low profile. To be effective, the Boston brace is required to be worn for up to 23 hours/day. The nighttime Charleston brace (Price, C. T. et al. "Nighttime Bracing for Adolescent Idiopathic Scoliosis with the Charleston Bending Brace", Spine Vol. 15, No. 12, pp. 1294–1299, 1990) must be worn 8 hours/night. The degree of support and the extent of corrective action provided by a brace depends on the location, magnitude, and direction of the pressures exerted relative to the location of the spine (Emans, J. et al. "The Boston Brace System for Idiopathic Scoliosis—Follow-up Results in 295 Patients", Spine, Vol. 11, No. 8, pp. 792–801, 1986).

However, it has been found that the constant pressure exerted by a brace may cause permanent deformation of the rib cage or the soft tissues directly under the pressure points. Also, it is believed that the brace's action is not primarily passive via direct mechanical forces on the spine, but that its effectiveness requires the active cooperation of the patient or person, (Dworkin, B. et al. "Behavioral method for the treatment of Idiopathic Scoliosis", Proc. Natl. Acad. Sci. Vol. 82, pp. 2493–2497, 1985) i.e., the patient or person uses their own muscles to reduce the spinal curvature as she or he holds their body away from the pressure points.

Therefore, it is recognized that monitoring the posture of, and active correction of the posture, the subject or patient is a useful aid to the treatment of various musculoskeletal conditions, such as scoliosis and spinal curvature, either on its own or in conjunction with other treatment methods and devices. Specifically, treatment approaches that rely less on mechanical correction and more on providing appropriate feedback to the subject may have considerable potential.

The monitoring of a subject's or patient's posture typically requires the actual taking of repeated measurements of the features of the trunk during waking hours, using these measurements to detect postural mal-alignment and signaling to the subject that a postural correction is required. In the specific area of monitoring subjects with spinal deformities, one or more features, such as the seven features noted above, must be measured and any differences from expected values determined. In the case when more than one feature is being monitored, information from some or all the features may need to be combined to signal the need for postural improvement.

Thus, the taking of actual measurements of these features on a constant basis is often a relatively impractical and cumbersome approach to monitoring and correcting posture. As a result, attempts have been made to develop various devices for monitoring posture and providing feedback with respect to that posture so that the subject can actively correct any undesirable features of the posture.

For instances, a technique described by Schroth et al. (Lehnert, C. S. "Introduction to the three-dimensional scoliosis treatment according to Schroth", Physiotherapy, Vol. 78 No. 11 pp. 810–815, 1992; Weiss, H. R. "The Progression of Idiopathic Scoliosis under the Influence of a Physiotherapy rehabilitation Programme", Physiotherapy, Vol. 78 No. 11, pp. 815–82, 1992) called rotational breathing attempts to actively correct the body shape. The continuous muscular training results in a re-education of the scoliotic posture into a corrected balanced posture. An electronic device called the micro-straight orthosis uses behavioral principles and therapeutic theory to help correct spinal deformity as well as cosmetic appearances. This device uses chest and torso cables and a microcomputer to continuously measure the length of the spine. If the length of the spine is different from the expected value, an audible tone signals the subject every second until correct posture is attained. Thus, one drawback of this device it that it provides feedback on the measured length of the spine only.

U.S. Pat. No. 3,582,935 issued Jun. 1, 1971 to Verhaeghe is directed at a device comprised of a belt connected to a triggering plate and a spring switch arm which close an electrical circuit when they come into contact with each other. The belt is placed snugly about the waist of the subject. If the subject permits his abdominal muscles to relax and thus be distended, the trigger plate will engage the switch arm, resulting in the closing of the electrical circuit. Closure of the electrical circuit activates an audible signal cautioning the subject to tense the relaxed abdominal muscles. This device is intended to signal the subject with respect to incorrect body posture, particularly in the abdomen. However, it would appear to have limited application to other features of incorrect posture.

U.S. Pat. No. 4,730,625 issued Mar. 15, 1988 to Fraser et, al. describes an article of apparel, that is worn by a subject which includes a posture sensor. The posture sensor is comprised of an elongated strip which fits into a horizontal or vertical pocket on the back of the article of apparel. Semiconductor strain gauges are mounted at the ends of these elongated strips. When the subject moves and a strain is applied to the gauges, the gauges produce an electrical signal which is proportional to the amount of strain applied. This patent specifically teaches a system for detecting changes in posture from the normal. However, many subjects with spinal deformities or abnormalities do not have a normally symmetric trunk so it is not sufficient to monitor changes of posture in the midline of the back only. For example, the angle formed by the apices of the scapulae and the horizontal is an important trunk feature to be monitored. Because the space between these bones is concave, the apparel of this invention will bridge this area of the back and mask the true extent of this particular trunk feature.

As stated, each of these devices only monitors a single parameter aspect or feature of posture. Further, these devices only, monitor a parameter in a single dimension or plane. Therefore, these devices may not be suitable for subjects having other postural abnormalities and they may not permit the subject to correct the deficient posture or abnormal features with any degree of accuracy. This is particularly so given the interplay of the features noted above, which may act together to produce the spinal deformity actually observed.

There is therefore a need in the industry for a relatively accurate method and a device, as compared to known methods and devices, for monitoring the position or orientation of one or more objects or subjects and providing feedback with respect to the position or orientation, in any dimension and preferably in three dimensions. Further, there is a need for a relatively accurate method and a device for monitoring the posture of a subject and providing feedback with respect to the subject's posture, such as by signaling when either a desirable or undesirable posture exists, so that a desirable posture can be established.

SUMMARY OF THE INVENTION

The present invention relates to a method and a device for monitoring the position or orientation of one or more objects or subjects and providing feedback with respect to the position or orientation, in any dimension, and preferably in three dimensions. Further, the invention is related to a method and a device for monitoring the posture of a subject and providing feedback with respect to the subject's posture, such as by signaling when either a desirable or undesirable posture exists, so that a desirable posture can be established.

In the apparatus form of the within invention, the invention is directed at a device for monitoring the position of a second point relative to a first point, the device comprising:

(a) a transmitter for locating at the first point for transmitting a transmitter signal;
(b) means for producing the transmitter signal;
(c) a receiver for locating at the second point for receiving the transmitter signal and for producing an output signal therefrom; and
(d) means for collecting the output signal so that the position of the second point relative to the first point can be determined therefrom.

The transmitter may be comprised of one or more transmitters. Further, the transmitter may be any suitable transmitter capable of performing the necessary functions, as described herein. Further, the transmitter may be comprised of a first transmitter loop and a second transmitter loop which is oriented in a different plane than the first transmitter loop, so that the transmitter transmits a first transmitter signal from the first transmitter loop and transmits a second transmitter signal from the second transmitter loop which are then received by the receiver to produce two output signals. The transmitter may also be comprised of a first transmitter loop, a second transmitter loop and a third transmitter loop, all of which are oriented in different planes, so that the transmitter transmits a first transmitter signal from the first transmitter loop, a second transmitter signal from the second transmitter loop, and a third transmitter signal from the third transmitter loop which are then received by the receiver to produce three output signals.

The receiver may also be comprised of one or more receivers. Further, the receiver may be comprised of any suitable receiver able to perform the functions described herein. Further, the receiver may be comprised of a first receiver loop and a second receiver loop which is oriented in a different plane than the first receiver loop, so that the transmitter signal is received by each of the first receiver loop and the second receiver loop to produce two output signals. The receiver may also be comprised of a first receiver loop, a second receiver loop and a third receiver loop, all of which are oriented in different planes, so that the transmitter signal is received by each of the first receiver loop, the second receiver loop and the third receiver loop to produce three output signals.

Where the transmitter is comprised of the first transmitter loop and the second transmitter loop and the receiver is comprised of the first receiver loop and the second receiver loop, the first transmitter signal and the second transmitter signal are each received by each of the first receiver loop and the second receiver loop to produce four output signals. Where the transmitter is comprised of the first transmitter loop the second receiver loop and the third receiver loop, the first transmitter signal and the second receiver loop and the third receiver loop, the first transmitter signal and the second transmitter signal are each received by each of the first receiver loop, the second receiver loop and the third receiver loop to produce six output signals.

Where the transmitter is comprised of a first transmitter loop, a second transmitter loop and a third transmitter loop, and the receiver is comprised of a first receiver loop and a second receiver loop, the first transmitter signal, the second transmitter signal and the third transmitter signal are each received by each of the first receiver loop and the second receiver loop to produce six output signals. Where the transmitter is comprised of the first transmitter loop, the second transmitter loop and the third transmitter loop, and the receiver is comprised of the first receiver loop, the second receiver loop and the third receiver loop, the first transmitter signal, the second transmitter signal and the third transmitter signal are each received by each of the first receiver loop, the second receiver loop and the third receiver loop to produce nine output signals.

Further, preferably, the first transmitter loop, the second transmitter loop and the third transmitter loop are all substantially mutually perpendicular to each other. Further, preferably, the first receiver loop, the second receiver loop and the third receiver loop are all substantially mutually perpendicular to each other.

As well, the transmitter signal producing means is preferably comprised of an oscillator which produces a variable transmitter signal. Any suitable oscillator for the purposes described herein may be used. Further, the transmitter signal producing means preferably produces the first transmitter signal, the second transmitter signal and the third transmitter signal, alternately in succession.

Further, the output signal collecting means preferably produces a feedback signal for indicating the position and orientation of the second point relative to the first point. The feedback signal may be comprised of any suitable devices or systems for providing a signal to the user of the device, however, the feedback signal is preferably comprised of sound, light, vibration or electrical stimulation. Alternatively, the feedback signal may be displayed on an oscilloscope.

In the preferred embodiments, the second point is comprised of a location on a human body.

Further, preferably, the receiver is comprised of at least a first receiver and a second receiver, each receiver comprising a first receiver loop, a second receiver loop and a third receiver loop, all of which are mutually perpendicular to each other, and wherein the first receiver is for locating at a first location on a human body and the second receiver is for locating at a second location on a human body, so that the relative position and orientation of the first point relative to the first location and the relative position and orientation of the first point relative to the second location can be compared.

In the method form of the invention, the invention is directed at a method for monitoring the position of a second point relative to a first point, the method comprising:

(a) producing a magnetic field from the first point;
(b) receiving the magnetic field at the second point and producing an output signal therefrom;
(c) determining the position of the second point relative to the first point by using the output signal.

The magnetic field may be comprised of a first magnetic field and a second magnetic field which are produced alternately in different directions from the first point. However, preferably, the magnetic field is comprised of a first magnetic field, a second magnetic field and a third magnetic field, each of which are produced alternately in different directions from the first point.

Further, the magnetic field may be received at the second point at two different positions. However, preferably, the magnetic field is received at the second point at three different positions.

As well, the method may be comprised of the following steps in the sequence set forth:

(a) producing a first magnetic field from the first point;
(b)) receiving the first magnetic field at three different mutually perpendicular positions at the second point and producing three output. signals therefrom;
(c) producing a second magnetic field from the first point in a different direction from the first magnetic field;
(d) receiving the second magnetic field at three different mutually perpendicular positions at the second point and producing three output signals therefrom;
(e) producing a third magnetic field at the first point in a different direction from each of the first magnetic field and the second magnetic field;
(f) receiving the third magnetic field at three different mutually perpendicular positions at the second point and producing three output signals therefrom; and
(g) determining the position and orientation of the second point relative to the first point by using the output signals.

Further, the method may be further comprised of the following steps after the determining step:

(h) comparing the position and orientation of the second point relative to the first point with a reference position and orientation; and
(i) producing feedback to indicate a discrepancy between the position and orientation of the second point relative to the first point and the reference position and orientation.

SUMMARY OF DRAWINGS

Embodiments of the invention will now be described with reference to the accompanying drawings, in which.

DETAILED DESCRIPTION

Figure 1:
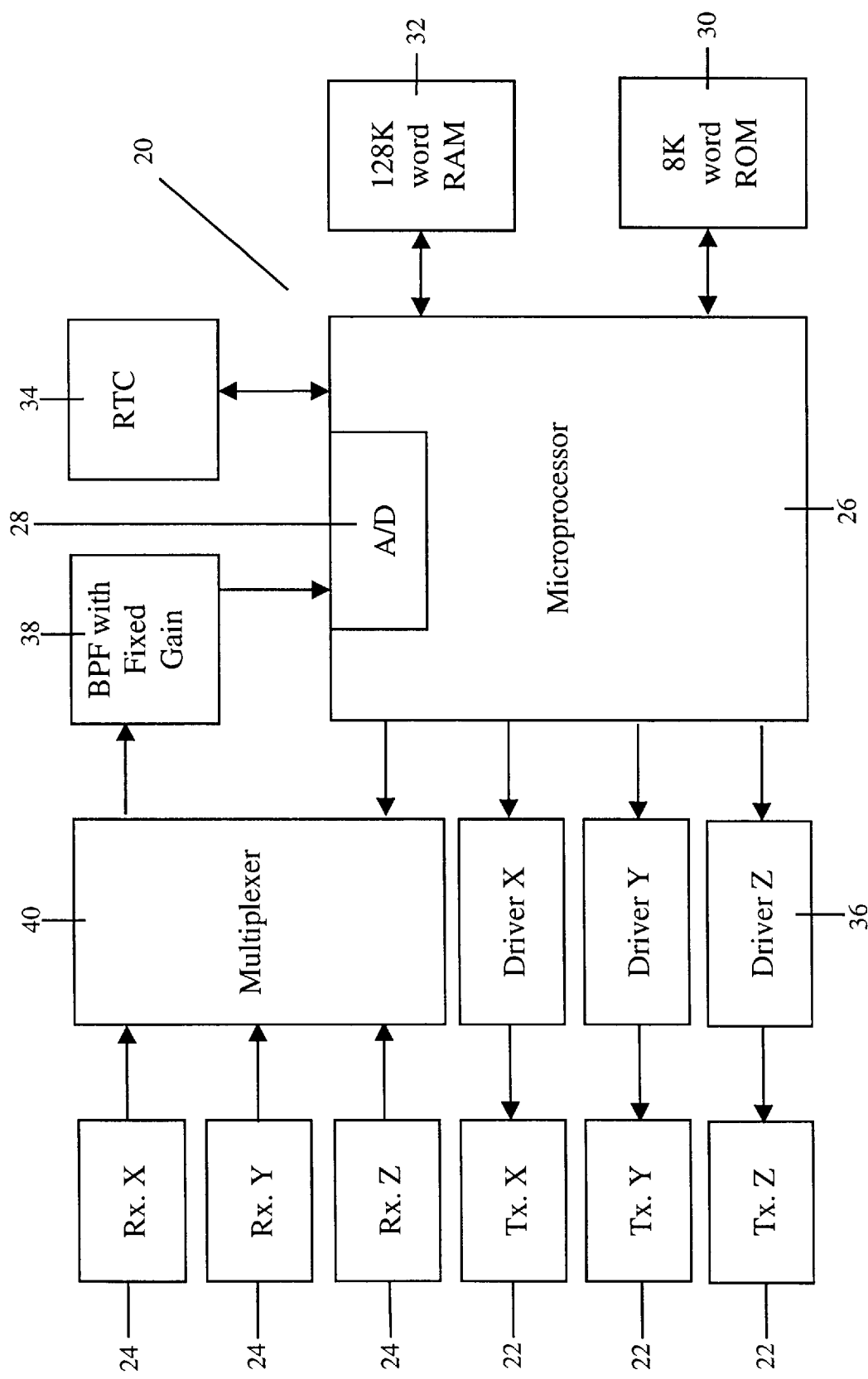
FIG. 1—is a schematic diagram of the preferred embodiment of the device of the within invention.

Referring to FIG. 1, this invention is directed at a system or device (20), and a method for monitoring at least one of the position and orientation of one or more objects or subjects and providing feedback with respect to the position or orientation, preferably in at least two dimensions. In the preferred embodiment, the device (20) is comprised of at least one transmitter (22) referred to in FIG. 1 by the designation Tx), preferably an electromagnetic transmitter, at least one receiver (24) (referred to in FIG. 1 by the designation Rx) and a microprocessor or microcontroller (26) which is attached to one or more objects or one or more subjects being monitored. The transmitter (22) and the receiver (24) may be attached directly or indirectly to an object or subject. Most preferably, The transmitter (22) is comprised of a fixed magnetic-dipole transmitting antenna and the receiver (24) is comprised of a freely moveable magnetic-dipole receiving antennae. The method of the within invention is preferably performed using the device (20).

It is believed that the theory of the operation of the device (20) is as set out below. Specifically, referinrg to FIG. 3, in the preferred embodiment utilizing an electromagnetic transmitter (22), to calculate the magnetic field generated from a square loop abcd (FIG. 3), the square loop abcd is divided into four finite lengths of wire. Each current-carrying wire produces a magnetic field at any point. Superimposing the magnetic field of the four wires into a square results in the magnetic field generated from a square loop (Cheng, D. K. "Field and Wave Electromagnetics", world student series 2nd Ed. Addison-Wesley, 1989). Assuming r >w and r<λ (where r is the distance between the transmitter (22) and the receiver(24), the magnetic fields generated from the wire ab and the wire cd cancel each other The magnetic field generated from the square loop abcd shown in FIG. 3 to the point (0,r,0) is described by Equation (1) as follows:

$$\vec{B} \approx -\vec{a}x\left(\frac{\mu_0 I w^2}{4\pi r^3}\right)$$ Equation(1)

Figure 3:
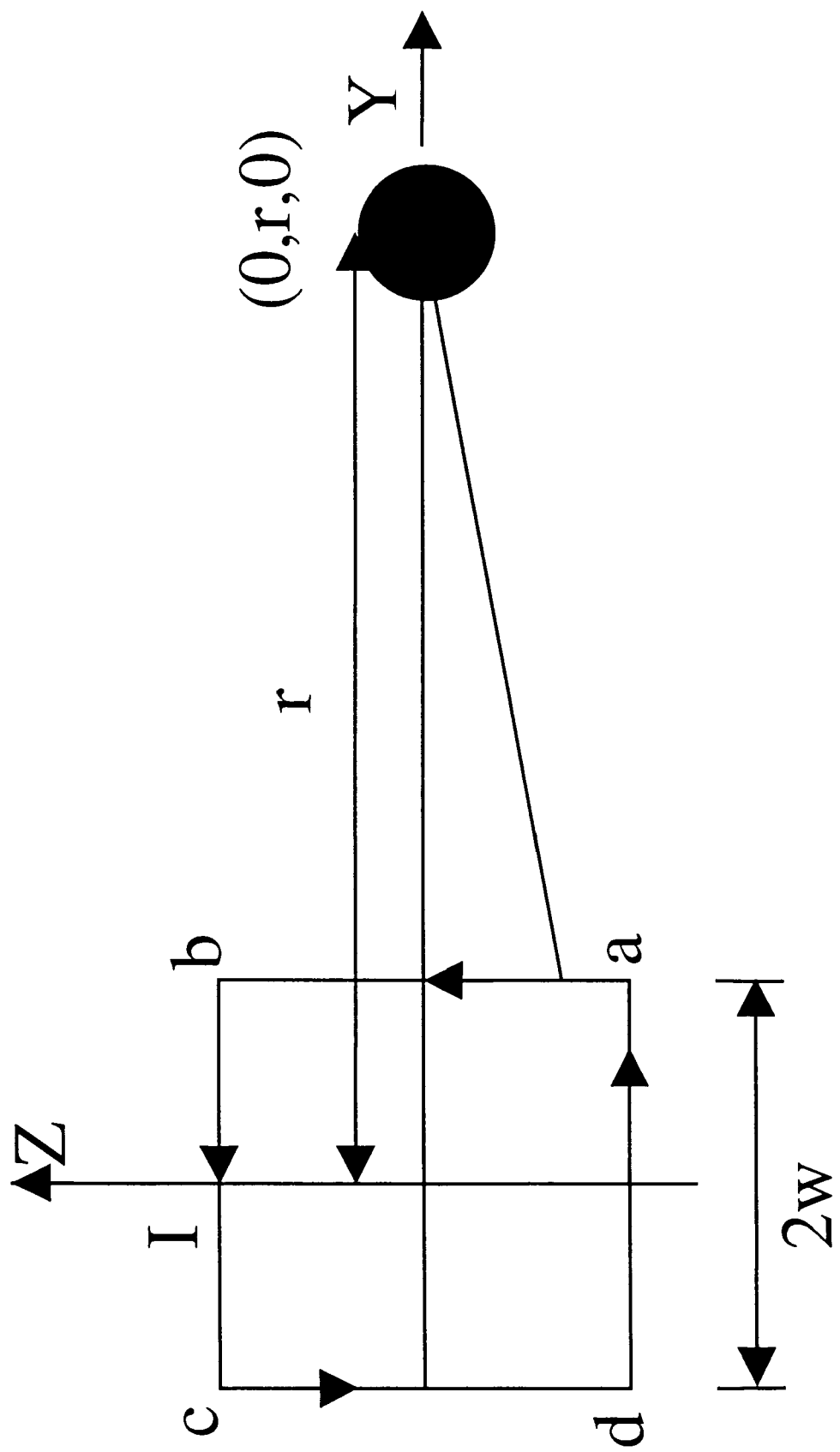
FIG. 3—is a magnetic field at $(0,r,0)$ from a square loop for the device shown in FIG. 1.
Figure 4:
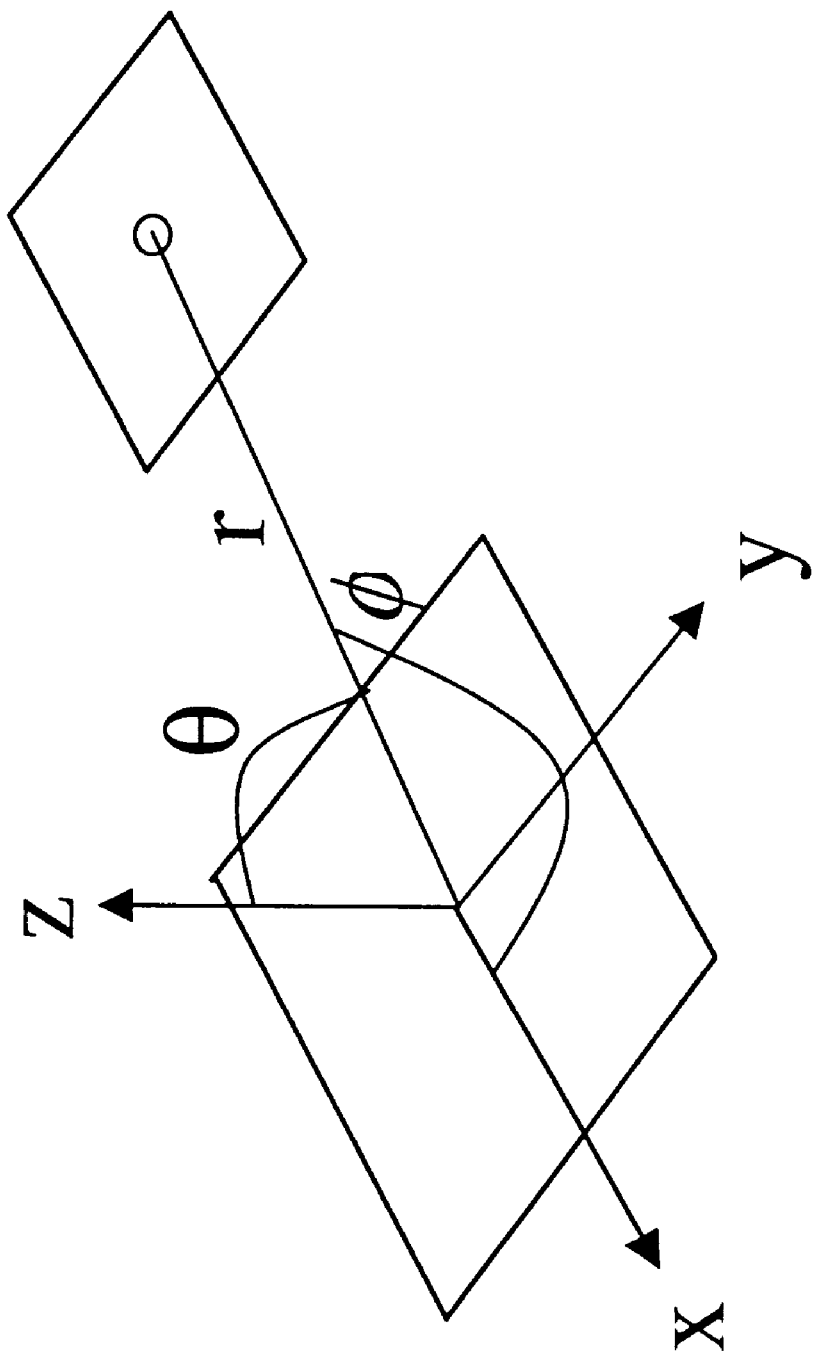
FIG. 4—is a magnetic field generated by the square loop shown in FIG. 3.

Referring to FIG. 4, the magnetic field generated from the square loop shown in FIG. 3 at general point (r, φ, θ) in polar coordinates (where θ is the angle of rotation) is given by Equation (2) as follows:

$$\vec{B} \approx \frac{\mu_0 M_0}{4\pi r^3}(\vec{a}_r 2\cos\theta + \vec{a}_\theta \sin\theta)$$ Equation(2)

Further, the following Equation (3) describes the magnetic flux generated from the transmitter (22), designated as 1 in the equation, to the receiver (24), designated as 2 in the equation, and wherein $N_1$ and $N_2$ are the number of turns in the transmitter (22) and the receiver (24) respectively and $S_2$ is the cross sectional area of the receiver (24):

$$\Phi_{12_{total}} = N_1 N_2 \int_{S_2} \vec{B}_1 \cdot \vec{d}s_2$$ Equation(3)

The following Equation (4) describes how the voltage (back emf) is related to the magnetic flux:

$$V_{e.m.f} = -\frac{d\Phi}{dt}$$ Equation(4)

The following Equation (5) describes the magnetic moment M0 where $S_1$ is the cross sectional area of the transmitter (22):

$$M_0 = IS_1$$ Equation (5)

Therefore, the relationship between the voltage and the distance between transmitter (22) and the receiver (24) is given by the following Equation (6):

$$V_{ii} = \frac{K_{ii}}{r^3} * \cos\theta + N_{ii}$$ Equation(6)

In Equation (6), K is a function of φ and is channel related. Further, $V_{ii}$ is the voltage on the channel transmitted from i and received on i and $N_{ii}$ is the noise picked up on the channel.

The following Equation (7) describes the relation between the angle of rotation and the voltage output:

$$\frac{V_{xy} - N_{xy}}{V_{xx} - N_{xx}} * \frac{K_{xx}}{K_{xy}} = \tan\theta$$ Equation(7)

The quality factor Q on the transmitter (22) can be calculated by the following Equation (8):

$$Q = \frac{\omega L}{R}$$ Equation(8)

The transmitting voltages on the capacitor C and the inductor L are described in the following Equation (9):

$$|V_L(j\omega)| = |V_C(j\omega)| = Q|V(j\omega)|$$ Equation (9)

The following Equations (10) and (11) describe the Q factor, and the current through the receiver (24):

$$Q = \omega RC$$ Equation (10)

$$|I_L(j\omega)| = |I_C(j\omega)| = Q|I(j\omega)|$$ Equation (11)

Referring to FIG. 1, in the preferred embodiment, the components of the device (20) may be separated into two systems or functional classifications: i) the programmable digital data acquisition system; and ii) the transmitter (22)—receiver (24) system with the associated circuitry. The data acquisition system is preferably comprised of any microcontroller or microprocessor (26) suitable for the specific purposes, and able to perform the necessary functions, as described herein. The microcontroller (26) provides for the programmability of the data acquisition system. Preferably, the microcontroller (26) is relatively small in size, such that it is readily portable, and has a relatively low power consumption. In the preferred embodiment, a microcontroller integrated circuit was chosen which has low power consumption and a built-in analog-to-digital (A/D) converter (28). Specifically, a Motorola MC68HC16 16-bit modular microcontroller integrated circuit is used.

Small size and low power consumptions are achieved by minimizing the number of integrated circuits (IC), and turning off the power for any IC not in use. Further, to reduce power requirements the read-only memory (ROM) (30) is a low-power CMOS integrated circuit which holds the control program. The static random access memory (RAM) (32), used to store the acquired data, is fabricated using an advanced low-powered CMOS device, designed for high-speed and low power applications. It is particularly well suited for battery backup of nonvolatile memory applications. Further, the device (20) is preferably further comprised of a programmable real-time clock (RTC) (34) which controls the sample duration and interval, and provides an interrupt to the microcontroller (26). Also, it can be programmed to be in a low-power STOP mode, except at the specific times when it is acquiring data. The block diagram of the device (20) is shown in FIG. 1.

Referring to FIG. 1, the MC68HC16 microcontroller (26) is comprised of a true 16-bit CPU, a system integration module, an 8/10-bit A/D converter (28), a queued serial module, a general-purpose timer, and a 1024-byte standby RAM (32). In this preferred embodiment, the device (20) is further comprised of a driver (36). Preferably, the driver (36) is comprised of a Wein Bridge Oscillator. The oscillator produces a sine wave signal to the transmitter (22), and a voltage follower (38) is used to avoid undue loading. Preferably, a fourth order Butterworth bandpass filter is used and is designed to have a high quality factor (Q). The fixed gain of the system is set so that a full range (0 to 5V) can be obtained. The multiplexer (MUX.) (40) is controlled by the microcontroller (26) to select the required channel. The A/D converter (28) is preferably set to 10 bit resolution and its resolution error is preferably +12.5 mV in the full range scale.

Figure 2:
FIG. 2—is a front view of a transmitter and a receiver of the device shown in FIG. 1.

Any transmitter (22) and receiver (24) may be used that are suitable for the purposes, and able to perform the functions, described herein. However, preferably both the transmitter (22) and the receiver (24) are comprised of ferrous materials. More particularly, the transmitter (22) and the receiver (24) are comprised of ferrite cubes with three mutually orthogonal loops as shown in FIG. 2. Any suitable dimensions and weights of the cubes may be used. However, the dimensions of the cube in the preferred embodiment are 2.0 cm for the transmitter (22) and 1.3 cm for the receiver (24) and their weights are 30 g and 10 g respectively. Preferably, these components are as small as possible and therefore, these components are preferably miniaturized where such miniaturization is possible or available.

In the preferred embodiment, the loop diameters are small relative to the distance (r) between the transmitter (22) and the receiver (24) so that each loop may be regarded as an infinitesimal dipole. Eight hundred turns of 36 AWG wire are preferably wound around the transmitter (22) in each direction, and 500 turns of 38 AWG wire are preferably wound around the receiver (24). Using larger diameter wire in the transmitter (22) results in a smaller resistance. Therefore, higher Q of the transmitting signal can be obtained. Using smaller wire in the receiver (24) results in a better pick up. The number of turns are dependent upon the size of the transmitter (22) and the receiver (24). The preferred number of turns was specifically chosen because of the preferred size of the transmitter (22) and the receiver (24). The operating range (distance) of the device (20) can be changed by altering the specification of the components (i.e., changing the number of turns, the size of the wire and/or the size of the core).

The transmitter (22) acts as a fixed magnetic-dipole transmitting antenna which produces a far-field component and a near-field component. The near-field intensity is dominant when the distance between the transmitter (22) and the receiver (24) is less than one wavelength ($\lambda$) (25 km) of the transmitting signal. Only the near-field component is considered. The near-field component is frequency independent and decreases by the inverse cube of the distance $1/r3$. Each loop of the transmitter (22) antenna is in turn excited with a driving signal identical in frequency and phase. A twelve kilohertz driving frequency was chosen in the preferred embodiment because that particular frequency is least affected by other EM (electromagnetic) signals. Each excitation produces a single axis transmitter dipole with three independent outputs at the receiver (24). Therefore, nine measurements (3 orthogonal loops×3 outputs) are available to solve for the six unknowns x, y, z for position and yaw, pitch, and roll for orientation.

Figure 5B:
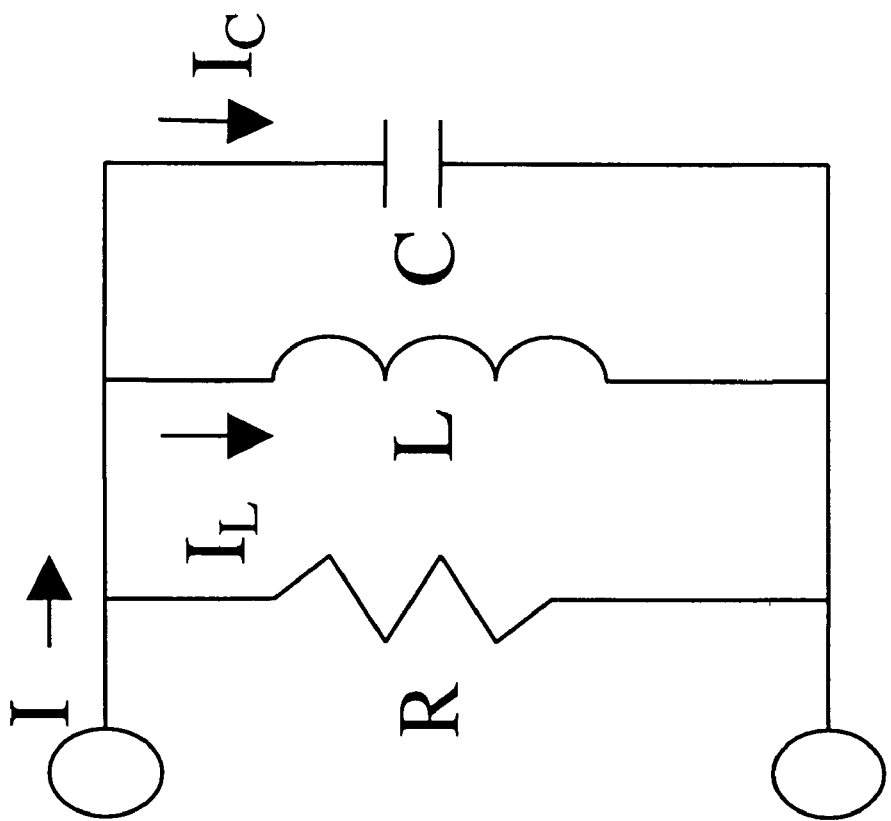
FIG. 5(b)—is a parallel RLC circuit for the receiver of the device shown in FIG. 1, wherein R is the resistor, L is the inductor and C is the capacitor.
Figure 5A:
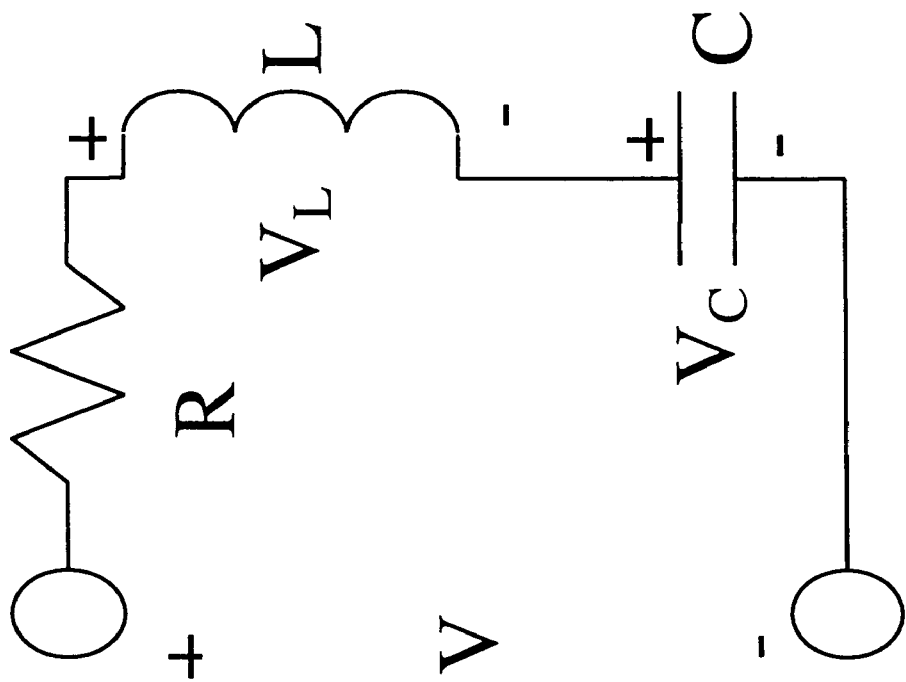
FIG. 5(a)—is an RLC circuit in series for the transmitter of the device shown in FIG. 1, wherein R is the resistor, L is the inductor and C is the capacitor.

The transmitter (22) uses the series resonant approach to transmit the signal, as shown in FIG. 5a, and the receiver (24) uses the parallel resonant approach to detect the signal, as shown in FIG. 5b.

Figure 6:
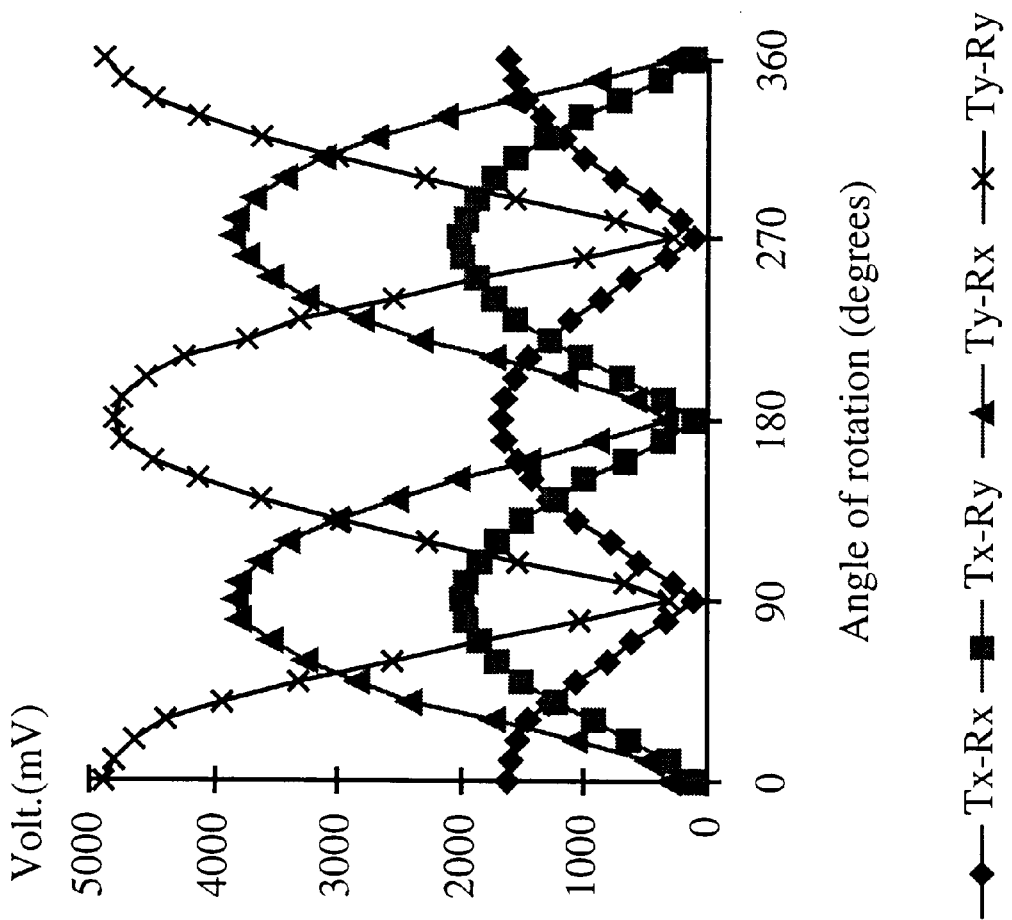
FIG. 6—shows the magnitude of the voltage at 4 channels (Tx-Rx, Tx-Ry, Ty-Rx and Ty-Ry, wherein T is the transmitter and R is the receiver) with respect to the rotation of the angle in the x-y plane.

The transmitter (22) receiver (24) system is preferably first calibrated by fixing the distance (r) between the transmitter (22) and the receiver (24). The distance for the calibration will depend on the range of distances required for the particular application of this device (20). At that distance, the receiver (24) is rotated in the x-y plane only from 0 to 360 degrees with 10 degree increments. The magnitude of the output signal is then read with an oscilloscope. Nine measurements (3 loops×3 outputs) are obtained each time. FIG. 6 shows the magnitude of the voltage at channels Tx–Rx (Transmit from x channel–Receive from x channel), Tx–Ry (transmit front x channel–Receive from y channel), Ty–Rx (Transmit from y channel) –Receive from x channel), and Ty–Ry (Transmit from y channel–Receive from y channel), with respect to the rotation, of the angle in the x-y plane in the preferred embodiment. The magnitude from Tx–Rz, Ty–Rz, Tz–Rx and Tz–Ry will vary for each application. The first calibration was at the minimum distance which provides the largest signal. The next test increases the distance between the transmitter (22) and the receiver (24). At each of the distances, the calibration steps were repeated.

Relating the above device (20) to use on subjects having scoliosis or other postural abnormalities or undesired features of posture, the device (20) is preferably a portable, low-power training device, as described above, to provide active feedback on the position and orientation of the subject, preferably in at least two dimensions, and more preferably, in three dimensions. This device (20) has applications for postural training and control. Experimental results have been compared to theory to determine the accuracy of the device (20). It has been found that the smallest distance and rotation angle that can be detected by the device (20) is 5 mm (range 30 to 45 cm) and 0.5 degrees respectively. This device (20) can provide feedback to scoliotic and other subjects to assist the subject in learning how to position himself properly with the ultimate aim to reduce their spinal deformity or undesirable posture.

Specifically, the device (20) and method of the within invention relate to monitoring locations of anatomical features that permit the calculation of the asymmetry of these and other anatomical structures. More specifically, the invention relates to a device (20) comprised of at least one transmitter (22), preferably an electromagnetic transmitter, at least one receiver (24) and a microprocessor (26) which is attached to the trunk of the subject whose posture is to be monitored. The transmitters (22) and the receivers (24) may be attached to the subject in any suitable manner permitting the functioning of the device (20) in the manner described herein. Specifically, the transmitters (22) and the receivers (24) may be attached directly to the skin using adhesive pads well described in the prior art or, in the case of the transmitter (22), may be secured in an elastic apparel worn around the trunk of the subject.

The receivers (24) are attached to one or more objects or one or more subjects being monitored. The transmitter or transmitters (22), microprocessor (26) and receiver or receivers (24) may be attached directly or indirectly to an object, objects, subject or subjects.

Signals, to the subject or the user of the device (20) may be continuous or activated only when certain definable orientations fall within or outside of a given range or ranges depending upon the specific application of the device (20). Signals concerning the position and orientation may be in the form of sound, light, vibration, electrical, output to a computer or any other available signaling system or device.

The device (20) may be powered by any suitable power source, compatible with the device (20), including battery or AC power.

As states above, monitoring posture has been used as an aid to the treatment of various musculoskeletal conditions such as spinal curvature. This requires repeatedly measuring features of the trunk during waking hours, using these measures to detect postural mal-alignment or undesirable features and signaling to the subject that a postural correction is required. In the specific area of monitoring subjects with spinal deformities, one or more features must be measured and any differences from expected values determined. In the case when more than one feature is being monitored, information from some or all the features may be combined to signal the need for postural improvement.

The within invention provides an electromagnetic device (20) comprised of a microcomputer that will monitor and measure one or more topographical features of the trunk related to the presence of abnormal spine curvature or other undesirable postural features. This includes but is not limited to monitoring and measurement of shoulder heights, shoulder angles, scapular heights, trunk shift, longitudinal waist contours and pelvic obliquity.

Further, the device (20) preferably analyzes these measurements in order to provide relative differences in the measurements or differences from preset conditions or measurements. Based on this analysis by the device (20), feedback is preferably provided to the subject. For example, if the intention is to return the angle of the shoulder to a more symmetric condition, then receivers (24) are placed on each shoulder to monitor the inclination of the shoulders relative to the transmitter (22) and return this information to the microprocessor (26). The microprocessor (26) then compares the shoulder angle measurements. It the normally aligned subject, this difference between the measurements will typically be zero. If the difference is greater than a preset difference then a signal or other form of feedback is transmitted to the subject.

Figure 7:
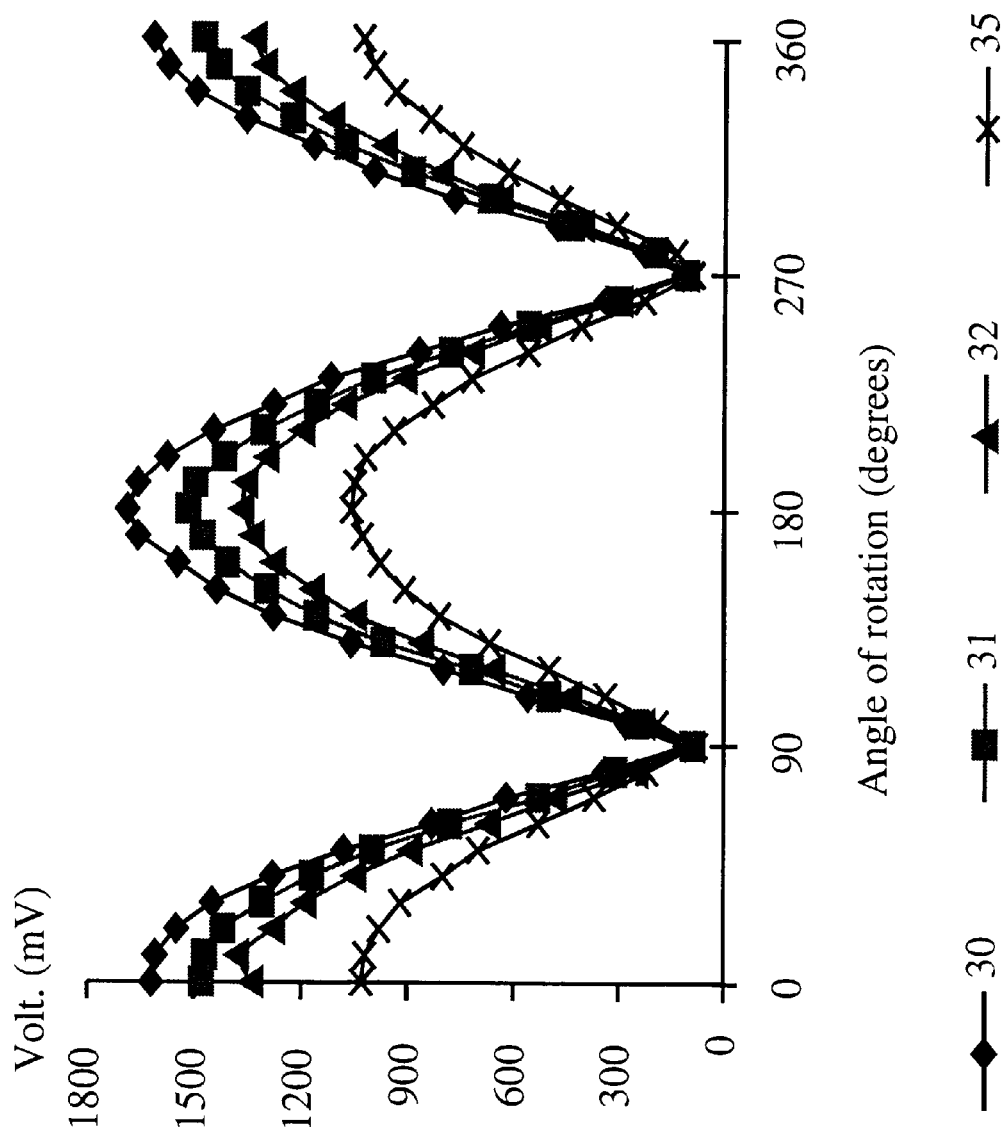
FIG. 7—shows the magnitude of the voltage at channel Tx-Rx at the distances of 30, 31, 32 and 35 cm with respect to the rotation of the angle in the x-y plane.
Figure 8:
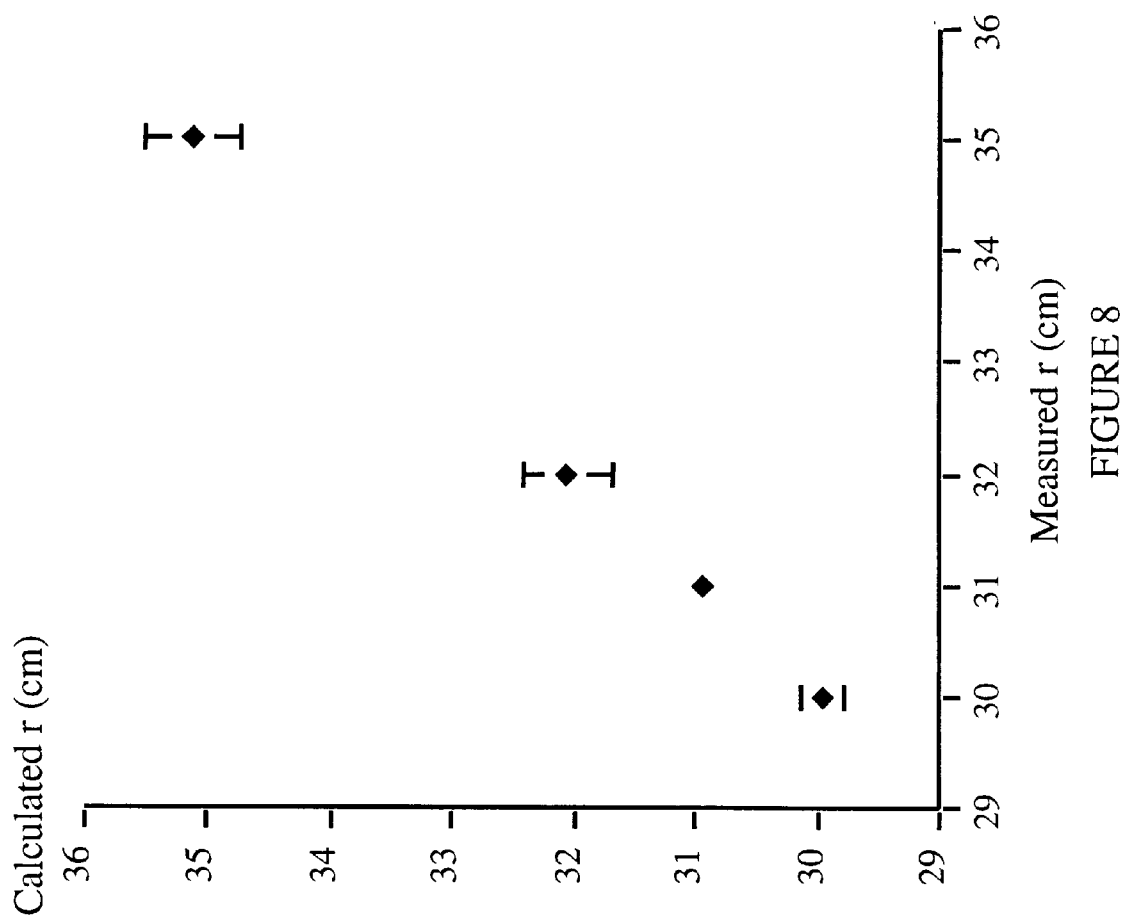
FIG. 8—shows the results of the calculated distance (with 1 standard deviation) as compared with the measured distance r.
Figure 9:
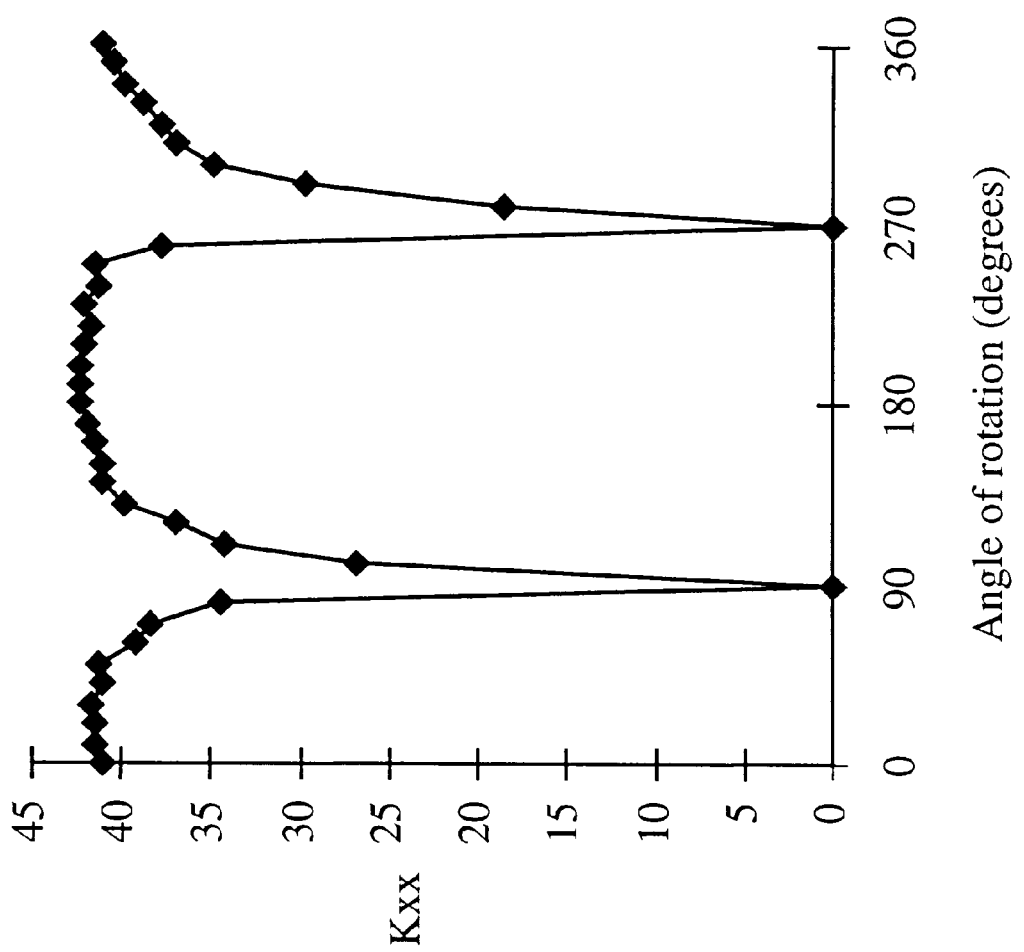
FIG. 9—shows the mean value of the function Kxx.
Figure 10:
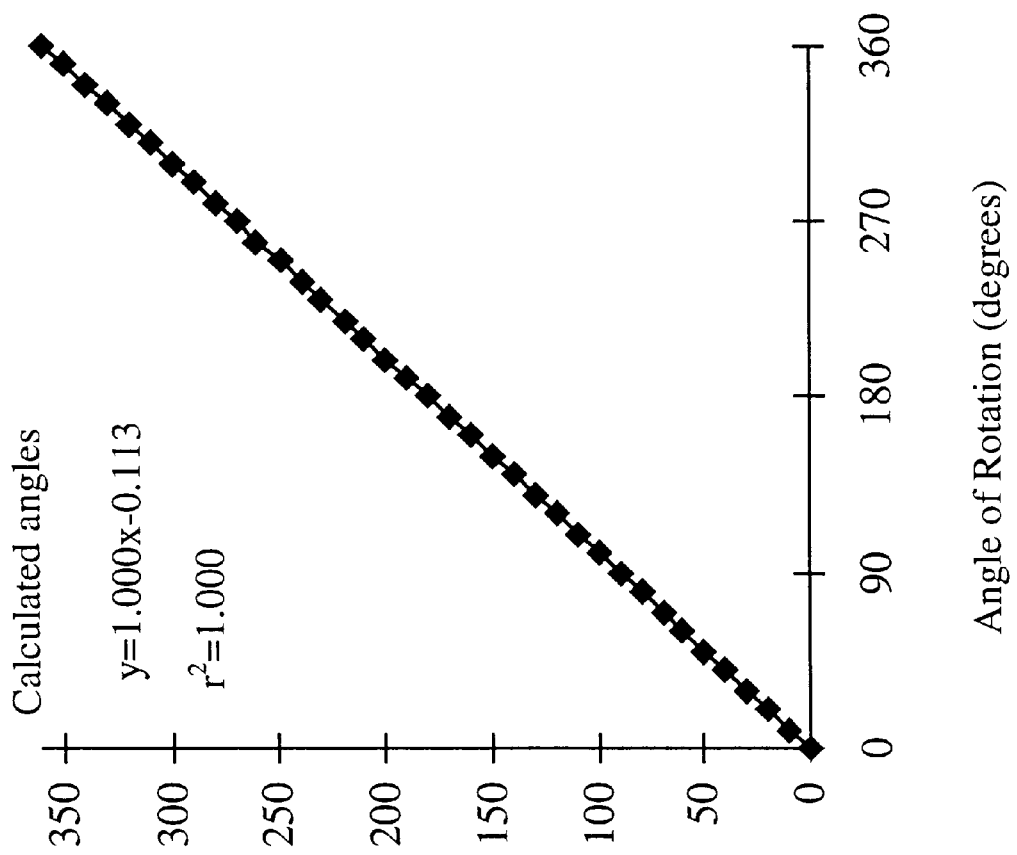
FIG. 10—shows the results of the measured angle of rotation as compared to the calculated angle of rotation.

When using the device (20) for a subject having a postural abnormality, such as scoliosis, the transmitter (22)-receiver (24) system are first calibrated, as previously described, by fixing the distance between the transmitter (22) and the receiver (24) at 30 cm. At that distance, the receiver (24) is rotated in the x-y plane only from 0 to 360 degree with 10 degree increments. The magnitude of the output signal is read with an oscilloscope. Nine measurements (3 loops×3 outputs) are obtained each time. As described above, FIG. 6 shows the magnitude of the voltage at channels Tx-Rx, Tx-Ry, Ty-Rx and Ty-Ry with respect to the rotation of the angle in the x-y plane. The magnitude from Tx-Rz, Ty-Rz, Tz-Rx and Tz-Ry were less than 200 mV. The magnitude of the voltage on the Tz-Rz channel at distance 30 cm was 2688 mV. The next test increases the distance to 30 cm, 31 cm, 32 cm and 35 cm between the transmitter (22) and the receiver (24). At each of the distances, the calibration steps are repeated. FIG. 7 shows the results obtained from the channel Tx-Rx at the distance 30 cm, 31 cm, 32 cm and 35 cm with respect to the angle of rotation in x-y plane in the preferred embodiment. FIG. 8 shows the accuracy on calculating the distance r from the received data upon testing and calibrating the preferred embodiment of the device (20). The mean values and the standard deviation of the calculated distance r, are 29.94 +0.18, 30.92+0.18, 32.06+0.37 and 35.11+0.38 cm. The smallest distance that can be detected is 5 mm in the distance range of 30 to 45 cm. FIG. 9 shows the variation of the function K with respect to the angle of the rotation. FIG. 10 shows the accuracy on calculating the angle from the received data. The average error in calculating the angle is $0.149°+0.36°$. The resolution on measuring the angle is $0.5°$.

Although the device (20) and the method of the within invention are preferably used for scoliosis correction, the device (20) and method have broader applications. For instance, a subject may use information from this device (20) to learn to utilize certain muscles to improve posture and reduce low back pain. Information from this device (20) may also be used to monitor how a person lifts and turns. Thus, the device (20) has applications in back care programs associated with safety in industry and rehabilitation for back injuries. Based on feedback from this device (20), a subject could train himself and his muscles to find and maintain correct positioning and posture. This has applications in back care programs associated with safety (prevention and occupational health and safety monitoring) in industry and rehabilitation for back injuries.

This invention also has application in a broader range of areas where monitoring parameters related to position, orientation or a subset of these parameters and relaying information about the parameters to a controller are desired. Information from the receivers (24) may be used to provide signals that indicate the alignment and relative position of points or objects in one or more dimensions, preferably three dimensions. The feedback response in this device (20) may be from a computer, machinery or an individual. This information can be used to initiate a signal and/or a response.

Further, this invention may have applications for robotics and virtual reality. This device (20) can be used to monitor or track positioning, and in particular three dimensional positioning, of one or more parts of a mechanism or of a body including but not limited to head, trunk, leg, foot, finger and/or hand. These applications may have many potential uses in entertainment, military and industry. This invention may also be used for applications related to but not limited to biomechanical analysis, graphic and cursor control, stereotaxic localization, anatomical measurements, simulations, kinematics, and biomechanics.

As well, this device (20) and method may have applications in guidance for 3-dimensional positioning and orientation. This device (20) and method may be used to assist in the assembling of equipment in unsafe environments, remote locations or assist in guidance in situations where alignment can not be monitored directly. This invention may also be used to guide equipment in surgery, for stereotaxic surgery or for providing information of the precise location of a probe of equipment for surgery. For instance, using computer graphics as feedback if one receiver (24) is on a moveable object and one receiver (24) is on a fixed or movable object, one can monitor the alignment.

The embodiments of the invention in which an exclusive property or privilege is claimed are defined as follows:

1. A method for monitoring the position of a movable second point located on an object relative to a movable first point located on the object, the method comprising:

(a) determining a plurality of preset reference signals which represent a preset three dimensional reference position of the second point relative to the first point;

(a) producing a first magnetic field, a second magnetic field and a third magnetic field alternately in different directions from the first point while the first point is moving in at least one dimension;

(b) receiving each of the first, second and third magnetic fields at the second point at three different positions while the second point is moving in at least one dimension and producing nine output signals therefrom;

(c) collecting the output signals so that the three dimensional position of the second point relative to the first point can be determined therefrom;

(d) comparing the output signals with the preset reference signals representative of the preset three dimensional reference position of the second point relative to the first point; and (e) producing at least one feedback signal for indicating variations between the output signals and the preset reference signals.

2. The method as claimed in claim 1 wherein the first, second and third magnetic fields are produced in substantially mutually perpendicular directions from the first point and wherein each of the first, second and third magnetic fields is received at the second point at three substantially mutually perpendicular positions.

3. The method as claimed in claim 2, wherein the object is comprised of a human body such that the first point and the second point each comprises a location on the same human body.

4. The method as claimed in claim 3, further comprising the steps of fastening the transmitter at the first point on the human body and fastening the receiver at the second point on the human body.

5. The method as claimed in claim 4, wherein at least one of the transmitter and receiver fastening steps is comprised of directly attaching at least one of the transmitter and the receiver to the human body by an adhesive.

6. The method as claimed in claim 4, wherein at least one of the transmitter and receiver fastening steps is comprised of securing at least one of the transmitter and the receiver to the human body by an elastic apparel.

7. The method as claimed in claim 2, further comprising the step, following the collecting step, of determining the three dimensional position of the second point relative to the first point by using the nine output signals.

8. The method as claimed in claim 2, further comprising the step, following the collecting step, of converting the output signals into a representation of the three dimensional position of the second point relative to the first point.

9. The method as claimed in claim 8, further comprising the step of converting the preset reference signals into a representation of the preset three dimensional reference position.

10. A device for monitoring the position of a movable second point located on an object relative to a movable first point located on the object, the device comprising:

(a) a mobile transmitter located at the first point on the object, wherein the mobile transmitter comprises a first transmitter loop, a second transmitter loop and a third transmitter loop, all of which are oriented in different planes, for transmitting a first transmitter signal from the first transmitter loop, a second transmitter signal from the second transmitter loop and a third transmitter signal from the third transmitter loop;

(b) means for producing the transmitter signals;

(c) a mobile receiver located at the second point on the object for receiving the transmitter signals, wherein the mobile receiver comprises a first receiver loop, a second receiver loop and a third receiver loop, all of which are oriented in different planes so that the first transmitter signal, the second transmitter signal and the third transmitter signal are each received by each of the first, second and third receiver loops, for producing nine output signals therefrom; and (d) means for collecting the output signals so that the three dimensional position of the second point relative to the first point can be determined therefrom, wherein the output signals collecting means compares the output signals with a plurality of preset reference signals which represents a preset three dimensional reference position of the second point relative to the first point and produces at least one feedback signal for indicating variations between the output signals and the preset reference signals.

11. The device as claimed in claim 10, wherein the first transmitter loop, the second transmitter loop and the third transmitter loop are all substantially mutually perpendicular to each other, and wherein the first receiver loop, the second receiver loop and the third receiver loop are all substantially mutually perpendicular to each other.

12. The device as claimed in claim 11, wherein the object is comprised of a human body such that the first point and the second point each comprises a location on the same human body.

13. The device as claimed in claim 12, further comprising first means for fastening the transmitter at the first point on the human body and second means for fastening the receiver at the second point on the human body.

14. The device as claimed in claim 13, wherein at least one of the first and second fastening means is comprised of an adhesive for directly attaching at least one of the transmitter and the receiver to the human body.

15. The device as claimed in claim 13, wherein at least one of the first and second fastening means is comprised of an elastic apparel for securing at least one of the transmitter and the receiver to the human body.

16. The device as claimed in claim 11, wherein the output signals collecting means determines the three dimensional position of the second point relative to the first point by using the nine output signals.

17. The device as claimed in claim 11, wherein the output signals collecting means converts the output signals into a representation of the three dimensional position of the second point relative to the first point.

18. The device as claimed in claim 17 wherein the output signals collecting means converts the preset reference signals into a representation of the preset three dimensional reference position.

19. The device as claimed in claim 11, wherein the transmitter signals producing means comprises an oscillator which produces a variable transmitter signal.

20. The device as claimed in claim 19, wherein the transmitter signal producing means produces the first transmitter signal, the second transmitter signal and the third transmitter signal alternately.

21. The device as claimed in claim 11, wherein the feedback signal is comprised of the presence or absence of sound, light, vibration or electrical stimulation.

22. The device as claimed in claim 11, wherein the feedback signal is displayed on an oscilloscope.

23. The device as claimed in claim 11, further comprising a computer memory, wherein the feedback signal is comprised of data indicating variations between the output signals and the preset reference signals and wherein the data is input into the computer memory.

24. The device as claimed in claim 11, wherein:

(a) the mobile receiver comprises a first mobile receiver and a second mobile receiver, each mobile receiver comprising a first receiver loop, a second receiver loop and a third receiver loop, all of which are mutually perpendicular to each other, for producing nine output signals therefrom;

(b) the second point comprises a first location on a human body and a second location on the same human body, wherein the first mobile receiver is located at the first location and the second mobile receiver is located at the second location; and (c) the output signals collecting means compares the output signals from each of the first and second mobile receivers with the plurality of preset reference signals and produces at least one feedback signal for indicating variations between the output signals and the preset reference signals.

* * * * *